(12) United States Patent
Lamoise et al.

(10) Patent No.: US 8,894,590 B2
(45) Date of Patent: Nov. 25, 2014

(54) INTERFACE PRESSURE MEASUREMENT SYSTEM

(75) Inventors: Michel Lamoise, Bessey les Citeaux (FR); Serge Lecomte, Dijon (FR); Julien Steinbrunn, Dijon (FR)

(73) Assignee: Laboratoires Urgo, Chenove (FR)

( * ) Notice: Subject to any disclaimer, the term of this patent is extended or adjusted under 35 U.S.C. 154(b) by 636 days.

(21) Appl. No.: 13/143,681

(22) PCT Filed: Jan. 13, 2010

(86) PCT No.: PCT/FR2010/050044
§ 371 (c)(1), (2), (4) Date: Sep. 14, 2011

(87) PCT Pub. No.: WO2010/081989
PCT Pub. Date: Jul. 22, 2010

(65) Prior Publication Data
US 2011/0319787 A1    Dec. 29, 2011

(30) Foreign Application Priority Data
Jan. 13, 2009    (FR) ...................................... 09 50147

(51) Int. Cl.
*A61B 5/03* (2006.01)
*A61B 5/117* (2006.01)
*A61B 5/103* (2006.01)
*A61B 5/00* (2006.01)

(52) U.S. Cl.
CPC ......... *A61B 5/103* (2013.01); *A61B 2562/0247* (2013.01); *A61B 5/445* (2013.01); *A61B 2562/0261* (2013.01); *A61B 5/6833* (2013.01)
USPC ........................................................ 600/587

(58) Field of Classification Search
CPC .................... A61B 5/6833; A61B 2562/0247; A61B 2562/046; A61B 5/01; A61B 17/1325; A61B 2562/164; A61B 5/0053; A61B 5/02438
USPC ................. 600/300, 301, 562, 573, 587, 595; 601/149–151
See application file for complete search history.

(56) References Cited

U.S. PATENT DOCUMENTS 3,736,436 A * 5/1973 Crites .......................... 307/400
4,186,732 A   2/1980 Christoffel
(Continued)

FOREIGN PATENT DOCUMENTS

DE   10 2007 020 247   6/2008
EP        1 884 226      2/2008
(Continued)

OTHER PUBLICATIONS

Deutsches Institut für Gütesicherung Und Kennzeichnung E.V. "Medical Compression Hosiery Quality Assurance RAL-GZ 387/1" (2008).

*Primary Examiner* — Sean Dougherty
(74) *Attorney, Agent, or Firm* — Hamre, Schumann, Mueller & Larson, P.C.

(57) ABSTRACT

The subject matter of the present invention is a system for measuring interface pressure exerted on the skin, that is in particular of use in compression therapy, characterized in that it comprises: —a supporting member bearing sensors, including at least two pressure sensors spaced out on the supporting member in order to make it possible to measure the pressure exerted at two predetermined positions; —an electronic system connected to the sensors and capable of acquiring the values simultaneously measured by these sensors; and in that each pressure sensor comprises a transducer element, which is preferably substantially flat, said transducer element having a surface intended to come into contact with the skin in the operating position, either directly or by means of a layer of a material covering said surface of the transducer, the elastic modulus of compression of said transducer or of said intermediate layer, measured at the surface intended to come into contact with the skin, being between 30 and 500 kPa, preferably between 80 and 400 kPa and more preferably between 200 and 400 kPa. Use: compression therapy.

46 Claims, 4 Drawing Sheets

(56) References Cited

U.S. PATENT DOCUMENTS

| | | | | |
|---|---|---|---|---|
| 5,320,596 | A * | 6/1994 | Catipovic et al. | 602/18 |
| 5,411,038 | A * | 5/1995 | Mollendorf et al. | 128/898 |
| 5,989,199 | A * | 11/1999 | Cundari et al. | 600/587 |
| 6,063,031 | A * | 5/2000 | Cundari et al. | 600/439 |
| 6,165,142 | A * | 12/2000 | Bar | 600/595 |
| 6,829,942 | B2 * | 12/2004 | Yanai et al. | 73/754 |
| 7,270,642 | B2 | 9/2007 | Ouchene et al. | |
| 7,297,094 | B2 * | 11/2007 | Starkey et al. | 482/134 |
| 7,333,841 | B2 * | 2/2008 | Maruo et al. | 600/316 |
| 7,618,384 | B2 * | 11/2009 | Nardi et al. | 601/149 |
| 7,947,003 | B2 * | 5/2011 | Bonnefin et al. | 601/150 |
| 8,007,436 | B2 * | 8/2011 | Katayama | 600/301 |
| 8,147,423 | B2 * | 4/2012 | Hashimshony et al. | 600/562 |
| 8,249,686 | B2 * | 8/2012 | Libbus et al. | 600/391 |
| 8,386,025 | B2 * | 2/2013 | Hoppe | 600/546 |
| 8,588,887 | B2 * | 11/2013 | Arneson et al. | 600/407 |
| 8,592,640 | B2 * | 11/2013 | Zepeda et al. | 602/58 |
| 2002/0173735 | A1 | 11/2002 | Lewis | |
| 2005/0090772 | A1 * | 4/2005 | Starkey et al. | 601/135 |
| 2005/0277852 | A1 * | 12/2005 | Shih et al. | 600/587 |
| 2006/0129216 | A1 * | 6/2006 | Hastings et al. | 607/115 |
| 2007/0038042 | A1 * | 2/2007 | Freeman et al. | 600/310 |
| 2007/0179482 | A1 * | 8/2007 | Anderson | 606/9 |
| 2007/0204698 | A1 * | 9/2007 | Fukutomi et al. | 73/728 |
| 2008/0214953 | A1 * | 9/2008 | Hashimshony et al. | 600/562 |
| 2008/0269606 | A1 * | 10/2008 | Matsumura | 600/438 |
| 2008/0275327 | A1 * | 11/2008 | Faarbaek et al. | 600/382 |
| 2009/0054980 | A1 * | 2/2009 | Ludlow et al. | 623/9 |
| 2009/0076336 | A1 * | 3/2009 | Mazar et al. | 600/300 |
| 2009/0171253 | A1 * | 7/2009 | Davenport | 601/2 |
| 2009/0187124 | A1 * | 7/2009 | Ludlow et al. | 601/47 |
| 2009/0209830 | A1 * | 8/2009 | Nagle et al. | 600/301 |
| 2009/0318793 | A1 * | 12/2009 | Datta et al. | 600/391 |
| 2010/0056966 | A1 * | 3/2010 | Toth | 601/134 |
| 2010/0113979 | A1 * | 5/2010 | Sarrafzadeh et al. | 600/587 |
| 2010/0152594 | A1 * | 6/2010 | Bhat et al. | 600/501 |
| 2010/0162832 | A1 * | 7/2010 | Brauers | 73/862.626 |
| 2010/0204632 | A1 * | 8/2010 | Lykke et al. | 602/54 |
| 2010/0234716 | A1 * | 9/2010 | Engel | 600/391 |
| 2011/0015496 | A1 * | 1/2011 | Sherman et al. | 600/301 |
| 2011/0015498 | A1 * | 1/2011 | Mestrovic et al. | 600/301 |
| 2011/0087182 | A1 * | 4/2011 | Stroebech et al. | 604/336 |
| 2011/0105872 | A1 * | 5/2011 | Chickering et al. | 600/365 |
| 2011/0105951 | A1 * | 5/2011 | Bernstein et al. | 600/573 |
| 2011/0105952 | A1 * | 5/2011 | Bernstein et al. | 600/573 |
| 2011/0270049 | A1 * | 11/2011 | Katra et al. | 600/301 |
| 2011/0282163 | A1 * | 11/2011 | Buja | 600/301 |
| 2011/0319787 | A1 * | 12/2011 | Lamoise et al. | 600/549 |
| 2012/0108917 | A1 * | 5/2012 | Libbus et al. | 600/301 |
| 2012/0330126 | A1 * | 12/2012 | Hoppe et al. | 600/391 |
| 2013/0030259 | A1 * | 1/2013 | Thomsen et al. | 600/301 |
| 2013/0060098 | A1 * | 3/2013 | Thomsen et al. | 600/301 |
| 2013/0096395 | A1 * | 4/2013 | Katra et al. | 600/301 |
| 2013/0226062 | A1 * | 8/2013 | Kloeppels et al. | 602/44 |

FOREIGN PATENT DOCUMENTS

| | | | | |
|---|---|---|---|---|
| FR | 2940904 A1 * | 7/2010 | | A61B 5/103 |
| GB | 2 322 556 | 9/1998 | | |
| GB | 2 439 750 | 1/2008 | | |
| GB | 2 445 760 | 7/2008 | | |
| WO | WO 00/72797 | 12/2000 | | |
| WO | WO 2004/107973 | 12/2004 | | |
| WO | WO 2006/030405 | 3/2006 | | |
| WO | WO 2006/040109 | 4/2006 | | |
| WO | WO 2006/058880 | 6/2006 | | |
| WO | WO 2006/079581 | 8/2006 | | |
| WO | WO 2006/094513 | 9/2006 | | |
| WO | WO 2006/103422 | 10/2006 | | |
| WO | WO 2007/079777 | 7/2007 | | |
| WO | WO 2007079777 A1 * | 7/2007 | | |
| WO | WO 2008/102308 | 8/2008 | | |
| WO | WO 2008102308 A2 * | 8/2008 | | |

\* cited by examiner

INTERFACE PRESSURE MEASUREMENT SYSTEM

The present invention generally relates to an interface pressure measurement system, in particular pressure exerted on the skin. It is particularly applicable in the medical field for compression therapy.

Compression therapy is recognized as an effective technique in the treatment of disorders associated with venous insufficiency, such as thromboses, edemas, lymphedemas or leg ulcers.

This therapy is based on the positioning of various compression devices such as compression stockings or bandages, the variable elasticity characteristics of which make it possible to choose the therapeutic pressure window to be used according to the patient and his pathologies.

A compression device such as a bandage must meet two objectives:

firstly, it must apply a suitable pressure upon placement; and on the other hand, it must maintain this pressure level for several days within a given therapeutic pressure range, so as to avoid having to reposition the bandage or to use a new one.

For a bandage to be effective, it is therefore not only necessary to have been correctly positioned but also for the patient to accept having to keep this bandage on for several days and to follow the recommendations of the clinical staff, for example by carrying out physical exercises, such as walking in the case of preventing venous thrombosis.

For maximum effectiveness, the compression system must be retained for 5 to 7 days and must apply a pressure gradually decreasing upwards along the leg, the resulting pressure gradient enabling the blood to be forced to rise upwards and not to stagnate. To give an example, the applied pressure may vary between a high value of around 30 to 40 mm of mercury at the malleoli of the ankle and a low value of around 15 to 25 mm of mercury in the upper part of the calf close to the knee.

Maintaining a pressure differential between the ankle and the calf is essential for treatment effectiveness.

However, the compression systems currently available do not include means for measuring this pressure differential. In addition, these systems do not make it possible to know the exact pressure applied or to follow its variation over the course of time, and consequently they cannot detect possible underpressure or overpressure problems.

Clinical staff are therefore incapable at the present time of monitoring or verifying whether the patient is following his treatment (physical exercise, wearing or removal of the compression system, etc.).

Therefore the use of these known compression systems is far from optimal.

There is therefore a strong demand, in the compression therapy field, for the development of a pressure measurement system for:

checking that the pressure exerted by the compression system is optimal not only at the moment of positioning it but also over the course of time;

checking that the ankle-calf pressure gradient remains optimal during the treatment;

detecting possible problems due to overpressures or underpressures; and recording the data over the course of time so as to allow the clinical staff to check that the patient has followed the treatment.

However, producing such a pressure measurement system comes up against many technical obstacles.

One of the main difficulties to be solved lies in developing a sensor for satisfactorily measuring the interface pressure exerted between the skin and the compression system.

Specifically, this sensor must:

be very sensitive so as to allow low pressures lying in the range varying from 1 to 120 mm of mercury, and in particular from 5 to 60 mm of mercury, to be measured with great accuracy, of the order of 1 mm of mercury;

be robust so as to be able to withstand a 100% overload (i.e. a pressure of 250 mm of mercury) without deterioration;

be very linear;

allow reliable measurements to be taken over a long period (several days); and be capable of operating both in static mode (when the patient is stationary) and in dynamic mode (when the patient is moving) and, consequently, the sensor must be capable of accurately measuring very low pressures at frequencies of the order of 1 hertz, corresponding to the variations to be recorded when a person is walking, and for very rapid variations in the applied pressure.

Thus, a satisfactory sensor, in the envisioned application, must have at the very least good sensitivity and linearity properties, both in static mode and in dynamic mode, for very low pressure measurements.

It has been determined that the linearity in the preferential measurement range (5-60 mm of mercury) must be ideally greater than 0.95 and even more preferably equal to or greater than 0.98. This is because if the sensor is not linear, to obtain easily exploitable results will require the use of an associated electronic system incorporating correction devices for making the electrical output signal proportional to the variations in the measured pressure values. The resulting system will be more complex and of higher manufacturing cost.

To enable very low pressures to be accurately measured for very rapid variations in the applied pressure, such as those observed when a person is walking, the surface of the sensor must advantageously have a low remanence, i.e. it must resume its initial shape and thickness in a very short time when the exerted pressure has ceased, in order to make a correct measurement when the next pressure is applied.

An ideal sensor must also be flexible and its surface must be able to adapt to the patient's morphology, to the nature and to the surface finish of the limb (bone, muscle, fat) to be treated.

The surface of the sensor must also adapt to the pressure applied by the compression system, which is not rigid. Specifically, this system consists of a band which, depending on the shape and the firmness of the limb to be treated, will deform not only the skin but also the sensor so as to give it a curved shape. This phenomenon is known as the "hammock effect", referring to the shape adopted by the sensor and the skin. The compressive forces induced by the bandage are partly absorbed because of this hammock effect and, under these conditions, a conventional pressure sensor detects practically nothing.

This is one of the reasons why a pressure measurement system comprising many sensors is difficult to develop in so far as each sensor would have to have specific properties and the associated electronic system would have been designed to manage a multitude of complex signals.

It is therefore necessary, because of the hammock effect, to provide a pressure sensor in which the curvature constraints have been minimized so as to ensure good distribution of the forces exerted on the measurement surface.

However, this must be accomplished without significantly increasing the thickness of the sensor so as to avoid impairing its intrinsic properties, as described above.

Furthermore, too thick or too rigid a sensor runs the risk of injuring the often fragile skin of the patient, in particular in the treatment of an ulcer.

As a result, the surface of an ideal sensor must possess contradictory specific properties so as to ensure both uniform and effective contact over this entire surface, by having a certain rigidity for limiting the hammock effect, and sufficient crush strength and specific flexibility so as to guarantee a reproducible linear signal over a long period.

As will be understood, the development of such a pressure measurement system satisfying all the conditions defined above is very complicated and this is one of the reasons why producing an interface pressure measurement system between a compression system and the skin, allowing simple routine use thereof, has hitherto remained an unsolved problem.

In this situation, the object of the present invention was to solve the technical problem consisting in supplying a pressure measurement system that can be used in particular in the context of treatment by compression therapy, which makes it possible for low pressures to be accurately measured over several days, both in static mode (stationary patient) and in dynamic mode (moving patient), and which is capable of delivering a reproducible linear signal that can be easily exploited by an electronic system and enables the effectiveness of the treatment to be controlled.

It has been discovered, and this constitutes the basis of the present invention, that it is possible to solve this technical problem in a satisfactory and particularly simple manner using at least two pressure sensors intended for simultaneously measuring the pressure being exerted at two predetermined locations on the patient to be treated and in which the material forming the active part of which, coming into contact with the skin in the envisaged preferential application, has a compressive elastic modulus within a selected range of values.

Thus, according to a first aspect, the present invention relates to a system for measuring the interface pressure exerted on the skin, especially useful in compression therapy, characterized in that it comprises:

a supporting member bearing sensors, including at least two pressure sensors placed apart on the supporting member, so as to be able to measure the pressure being exerted at two locations, one of which is predetermined; and an electronic system connected to the sensors and capable of acquiring the values simultaneously measured by these sensors, and in that each pressure sensor comprises a transducer element, which is preferably substantially flat, said transducer element having a surface intended to come into contact with the skin in the use position, either directly or via an intermediate layer of a material covering said surface of the transducer, the compressive elastic modulus of said transducer or of said intermediate layer, measured at the surface intended to come into contact with the skin, being between 30 and 500 kPa, preferably between 80 and 400 kPa and more preferably between 200 and 400 kPa.

According to one particular feature of the invention, the material constituting said aforementioned intermediate layer is chosen from:

cellular materials, such as particularly foams, preferably hydrophobic foams, such as for example foams made of crosslinked polyethylene or foams made of polyurethane, silicone, polyvinyl chloride, ethylene-propylene diene copolymer or neoprene;

gels, preferably hydrophobic gels, such as for example silicone gels or polyurethane gels; and compounds based on thermoplastic, preferably hydrophobic, polymers, such as for example compounds consisting of triblock polymers and a plasticizer.

According to another particular feature of the invention, each pressure sensor is substantially flat and chosen from resistive sensors, piezoelectric sensors, Hall-effect magnetic sensors and capacitive sensors.

According to another particular feature of the invention, the aforementioned electronic system comprises:

an onboard device connected to the supporting member, preferably by being fixed thereto, and serving for the acquisition and processing of the values measured by the pressure sensors, said device comprising means for transmitting said values measured by the sensors; and a remote device comprising:

communication means compatible with the transmission means of the onboard device and at least transmitting the data from the onboard device to the remote device, and a processing circuit connected to a display device.

The compression systems currently available also suffer from the drawback of not being able to adapt to the patient's morphology (size of the leg, size of the calf) and to the change in this morphology over the course of time, as for example in the case of edema.

In this context, the object of the present invention is also to solve the technical problem consisting in delivering a pressure measurement system that can adapt to the morphology of the patient and to the change in his pathology.

To solve this second technical problem, and according to a first preferred variant, the supporting member of the interface pressure measurement system according to the invention is extensible.

The design itself of an extensible measurement system with incorporated electronics poses many problems to be solved.

The first difficulty lies in developing a system in which the functionalities of the electronic circuit and the conducting tracks thereof, which connect the various functional elements (sensors, microprocessor, battery, etc.), are not altered when the system extends.

Likewise, these functional elements must not become disconnected from the supporting member when the latter extends.

Finally, the electronic circuit must possibly be protected so as, where appropriate, it can be partly or completely reused.

These difficulties have been solved by various additional features of the invention which will be explained in detail below.

Another object of the invention is to solve a third technical problem.

This is because, in certain cases, in particular in the case of the treatment of a chronic wound of the ulcer type, the use of a compression system faces the additional problem of how to monitor the area to be treated, in this case the wound, which is in fact covered by an absorbent dressing, itself concealed by the bandage of the compression system.

If, during the treatment, the level of exudation from the wound becomes greater than the absorption capacity of the dressing, the exudates spill over the edge of the wound. This may result, if this phenomenon is not rapidly detected, in the maceration of the wound and impairment of the perilesional skin, slowing down or impairing the ulcer healing process. In addition, contact between the bandage and the exudates may cause the mechanical properties of the bandage, and consequently its effectiveness, to deteriorate. Furthermore, the appearance of stains on the bandage may induce fear and psychological problems for the patient, which may result in him refusing to use a bandage again.

Moreover, during very hot weather, swelling of the legs, thereby modifying the pressure applied by the system, and the patient very often tends to remove the bandage.

Measuring the moisture and/or temperature beneath the bandage, in parallel with the pressure measurement, would therefore make it possible to improve the overall effectiveness of the treatment and allow the placement of the bandage to be adapted to the change in environment of the area to be treated.

Thus, to solve this third technical problem, and according to a second preferred variant of the invention, the supporting member further bears:

at least one moisture sensor; and/or
at least one temperature sensor.

According to a second aspect, the present invention relates to a restraint or compression kit consisting of a restraint or compression system and of an interface pressure measurement system as defined above.

DETAILED DESCRIPTION OF THE INVENTION

The invention will be better understood on reading the following explanatory description with reference to the appended drawings in which.

The Supporting Member

In the context of the present invention, the supporting member of the pressure measurement system may be made of any flexible material able to be made in sheet form and capable of deforming so as to follow the shape of that part of the body to be treated, for example a leg.

Such a material may for example be:
a fabric material, such as a woven, a nonwoven, a knit or a 3D fabric;
a cellular material, such as a foam;
a film;
a complex combining two of these materials;
a polymer matrix, such as a silicone gel.

As examples of complex materials, mention may be made of complexes consisting of the combination of a nonwoven and a film. Such materials may be produced by techniques well known to those skilled in the art, for example by application of an adhesive, by hot calendering or by ultrasonic complexing.

In the context of compression therapy, in particular for treating leg ulcers, it is important for the interface pressure measurement system not to impair the patient's skin, which is often weakened or in a very poor state, in particular around the ulcer.

The supporting member must therefore be thin, flexible and above all nonocclusive, that is to say it must have a water vapor permeability, measured according to the EM-13726 standard, equal to or greater than 1000 $g/m^2/24$ h.

In the context of the present invention, preferred examples of supporting members are polyurethane nonwovens and films.

According to one particularly preferred embodiment of the invention, the supporting member is extensible, preferably anisotropically extensible.

For this purpose, among the materials described above, it will be preferable to choose those that have an extensibility of around 10 to 20% in the longitudinal direction and an extensibility of around 3 to 12% in the transverse direction. It has been found that an extensibility of around 10 to 20% in the longitudinal direction makes it possible to cover, using one or two products, all patient morphology types.

It is also preferable to use an extensible material that has a low modulus of elasticity so as to be able to reconcile the advantages of extensibility with the capability of the supporting member to adhere to the skin, if said supporting member is coated with adhesive in order to facilitate the placement thereof.

Indeed, the lower the modulus of elasticity of the extensible material, the lower its restoring force. A supporting member having a relatively low modulus of elasticity, for example around 40 N/cm or less, may thus remain in extension for a time long enough for the clinical staff to be able to place the compression system on said supporting member easily.

According to a preferred variant of the invention, this low modulus of elasticity may be obtained by forming holes or empty areas in the extensible material constituting the supporting member. Of course, these holes or empty areas will be placed on the supporting member at suitably chosen locations so as not to impair, as it is being extended, the electronic connections and the conducting tracks possibly present thereon.

As examples of particularly preferred extensible materials, mention may be made of nonwovens or films based on polyurethanes, polyetheresters (in particular the products sold under the names HYTREL® or ARNITEL®), polyamides or polyetheramides.

Pressure Sensors

The interface pressure measurement system according to the invention comprises an array of sensors borne by the supporting member described above, including at least two pressure sensors placed apart on the supporting member, so as to be able to measure the pressure being exerted at two locations, one of which is predetermined.

The compression therapy is applied in most cases to the lower limbs.

Figure 1:
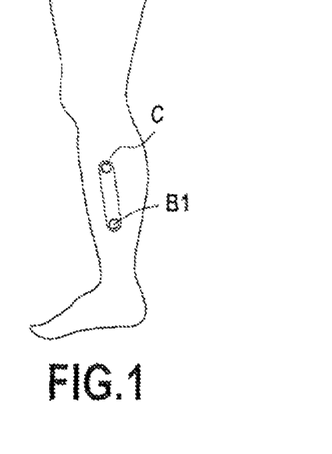
FIG. 1 schematically illustrates an interface pressure measurement system according to one embodiment of the invention, this being placed on a leg, and shows the points B1 and C between which the pressure differential is measured.

As an example, FIG. 1 therefore shows a system designed to be placed on a leg.

In this case, the two aforementioned pressure sensors will be advantageously fixed to the supporting member, at locations chosen in such a way that these sensors are placed respectively in the use position of the measurement system:

on the one hand, at a predetermined location such as the area referenced B1, where the Achilles tendon attaches to the calf muscle (about 10 to 15 cm above the malleoli); and on the other hand, in any region lying "downstream" of the area B1 (i.e. above the area B1, up along the leg), preferably in the area referenced C where the perimeter of the calf reaches its maximum.

The effectiveness of a compression system depends in fact on maintaining a pressure gradient between these two areas, the pressure in the area B1 having to be greater than the pressure in the area located downstream of the latter so as to guarantee that blood is forced upward and does not stagnate. Consequently, it is extremely important to be able to measure the pressure in these two areas.

Each pressure sensor advantageously meets specific geometric criteria (surface area and thickness) and specific metrology requirements (sensitivity and precision of the order of 1 mm of mercury and reproducibility of the measurements over several days).

Preferably, each sensor must be capable of withstanding a 100% overload without being damaged, i.e. a pressure of 250 mm of mercury.

To meet these constraints, it will be preferable to choose a pressure sensor in which the active part (a transducer optionally combined with an intermediate layer covering it):

is substantially flat;

has a thickness of 3 mm or less under a stress of 20 mm of mercury;

has a surface area of between 0.25 and 3 $cm^2$; and makes it possible to measure an interface pressure accurately over a range varying from 1 to 120 mm of mercury and in particular 5 to 60 mm of mercury.

Thus, an optimum pressure sensor has a linearity of greater than 0.95, preferably equal to or greater than 0.98, over the range from 1 to 120 mm of mercury and in particular from 5 to 60 mm of mercury.

To ensure reliable and reproducible measurements over time, the inventors have also determined, and this constitutes an essential feature of the invention, that the constituent material of the transducer or of the intermediate layer covering it must have a compression elastic modulus measured on the surface intended to come into contact with the skin of between 30 and 500 kPa.

This compression elastic modulus may be measured using a tensile testing machine fitted with compression plates according to the procedure described in the ISO 844 (2007) standard.

Preferably, the constituent material of the transducer or of the intermediate layer covering it will have a compression elastic modulus of between 80 and 400 kPa and more preferably between 200 and 400 kPa.

Any type of pressure sensor, with the exception of pneumatic sensors, may be used in the context of the invention.

The following sensors may thus be mentioned: resistive sensors, piezoelectric sensors and capacitive sensors, the electrical properties of which vary as a function of the pressure exerted, and magnetic sensors that operate according to the Hall effect.

In general, such sensors comprise:

on the one hand, an active part consisting of a transducer element capable of converting the pressure into a signal; and on the other hand, a nonactive part comprising conducting contacts or tracks capable of transmitting the signal output by the transducer to a processing unit.

In the context of the present application, the term "pressure sensor" therefore denotes the combination of a transducer and the aforementioned conducting contacts or tracks.

In the pressure sensors used according to the invention, the transducer directly converts the pressure that is applied to it into a signal, for example an electrical or magnetic signal, by converting a variation in one of the intrinsic physical characteristics of the transducer element such as, in particular its resistance, its capacitance, its electric field or else its QT (quantum tunneling) effect.

In these sensors, the transducer element, unlike pneumatic sensors, comprises neither gas nor liquid.

It should be noted that the use of pneumatic sensors cannot be envisaged in the context of the present invention:

firstly because such sensors are generally expensive, bulky and complicated; and secondly because their reliability is made uncertain owing to possible variations, for example due to the effect of temperature, in the properties of the gas or liquid that they contain and risks of leakage should the membrane enveloping this gas or liquid rupture.

Among resistive sensors that can be used in the context of the present invention, the sensors sold by Tekscan under the name FLEXIFORCE® and those sold by International Electronics and Engineering (IEE) under the name FSR® may be mentioned. Particularly, the sensors sold by IEE under the name FSR® will be preferred.

Whatever the type of sensor used, taken from those mentioned above, the surface and the thickness of these sensors will have to be modified by the addition of an intermediate layer in order to optimize the contacts between the transducer, the skin and the compression system so as to avoid the hammock effect and thus ensure a linear and reproducible measurement over time.

The sensors sold by IEE are force-sensing resistors. Their structure is extremely simple. It is a multilayer structure formed from two sheets of polymer laminated together which enclose two electrodes and a resistor. The higher the pressure applied to this structure, the more their resistance decreases. These sensors are temperature-resistant and resistant to chemicals and moisture. The technologies and the implementation of such sensors are for example described in the patent applications WO 2006/79581 and WO 2006/58880 from the company IEE.

To optimize the operation of these known sensors and obtain the ideal compression elastic modulus, that face of the transducer coming into contact with the skin must be covered with a relatively thick layer of a material that has a compressive elastic modulus of between 30 and 450 kPa.

These known sensors are flat, rigid and very thin, so that they can be directly used in the envisaged application.

If necessary, both faces of the transducer may be covered with identical or different materials, in particular materials having a compressive elastic modulus of between 30 and 500 kPa. This enables the negative effect of the pressure applied by the compressive system on the surface of the sensor, on the opposite side to the skin, to be more significantly reduced and thus enables better sensitivity and linearity of the sensor to be achieved.

However, in the context of the present invention, a sensor which is overly thick in its active part (the transducer covered with an intermediate layer) for example, the thickness of which is greater than 5 mm, should be avoided as this could make it difficult to fix it to the supporting member and could damage the patient's skin, which is often weakened.

In other words, the final structure of the sensor, and in particular the thickness of its active part, will be chosen by seeking the best compromise between its good compressibility and its sensitivity. Thus, if it is sought to measure low pressures and low pressure variations, it will be preferential to use a sensor, only the face of the transducer of which, coming into contact with the skin, is covered with a material having a compression elastic modulus of between 30 and 500 kPa and in particular between 200 and 400 kPa.

Among the materials that can be used to obtain such a compression elastic modulus, mention may be made of cellular materials, such as for example physically crosslinked polyethylene foams and in particular the foams of the ALVEOLIT range sold by Alveo or those sold by Trocelen under various references. These foams exhibit excellent chemical resistance and are inert to water.

Polyurethane foams, silicone foams (for example those sold by Poron under the references UL94HF or UL94VO), PVC (polyvinyl chloride) foams, EPDM (ethylene-propylene diene monomer) foams and neoprene foams may also be mentioned.

All these foams may be open-cell or closed-cell foams.

In the context of the present invention, it will be preferable to use a hydrophobic foam so as to prevent transpiration or exudates from the wound modifying their elastic properties, their density, their compression modulus or even their thickness, and it will be even more preferable to use a hydrophobic foam without a plasticizer so as to avoid any migration of toxic substances on the skin or in the wound.

In general, foams will be used that have a thickness of between 0.3 and 5 mm, preferably between 0.5 and 1.5 mm, and a density between 25 and 250 g/m$^3$, which will preferably be combined with transducers having a thickness of less than 0.8 mm, preferably less than 0.5 mm and even more preferably less than 0.3 mm.

According to the currently preferred embodiment of the present invention, each pressure sensor is an FSR® sensor comprising a transducer having a thickness of 0.4 mm and an area coming into contact with the skin at 2.27 cm$^2$ and bearing a polyurethane foam (sold by Poron).

According to other embodiments of the invention, this same FSR® sensor was covered with the following intermediate layers:
  a) a layer based on a mixture consisting of thermoplastic polymers and a plasticizer.
  This mixture consisted of:
  88% by weight of a triblock copolymer sold by Kraton under the name Kraton® G1651; and
  12% by weight of a mineral oil sold by Shell under the name Ondina® 917.
  This mixture was deposited in the form of a layer having a thickness of 4.24 mm on the aforementioned FSR® sensor.
  The elastic modulus of this layer was 240 kPa;
  b) a layer based on a polyurethane foam sold by Poron under the reference 4701-50-30031-04, having a black color.
  Fixed to an aforementioned sensor FSR®, using a double-sided adhesive 90 µm in thickness (acrylic adhesive/polyethylene terephthalate/acrylic adhesive), was a 0.8 mm-thick layer of the aforementioned foam.
  The compression elastic modulus of this foam layer was 380 kPa;
  c) a layer based on a polyurethane foam sold by Poron, blue in color.
  Fixed to an aforementioned FSR sensor, using a double-sided adhesive 90 µm in thickness (acrylic adhesive/polyethylene terephthalate/acrylic adhesive), was a 1.45 mm-thick layer of the aforementioned foam.
  The compression elastic modulus of this foam layer was 380 kPa; and
  d) fixed to each of the two faces of an aforementioned FSR® sensor, using a double-sided adhesive 90 µm in thickness (acrylic, adhesive/polyethylene terephthalate/ acrylic adhesive), was a 1.45 mm-thick layer of the foams described in b) and c) above.

According to other embodiments of the invention, the FSR® sensor in the embodiments described above was replaced with a FlexiForce sensor with the reference 1-617-464-4500, sold by Tekscan.

In all cases, the sensors thus modified proved to be satisfactory for achieving the desired results.

These cellular materials are fixed to the transducer of the sensor using known techniques, for example by hot calendering, by ultrasound, if the components are meltable, or by adhesion.

Preferably, these cellular materials are fixed by adhesion using a double-sided adhesive, for example an acrylic-based adhesive, preferably having a thickness of less than 200 µm, and even more preferably less than 100 µm.

Among other materials for adjusting the compression elastic modulus of the active surface of the sensor coming into contact with the skin, mention may also be made of gels, and in particular silicone gels or polyurethane gels. As in the case of foams, it will be preferable to use hydrophobic gels so that their properties are not impaired by transpiration or exudates.

Mention may also be made of compounds consisting of thermoplastic polymers and a plasticizer. These thermoplastic polymers will be especially triblock polymers, such as in particular the acrylic triblock polymers termed by Kuraray "LA polymers", triblock polymers of the ABA type in which A represents styrene units and B represents butadiene, isoprene, ethylene-butylene or ethylene-propylene units, such as the products of the KRATON G and KRATON D ranges sold by Kraton, the latter products being able to be combined with a mineral oil.

Such compounds of thermoplastic polymers and a plasticizer are well known to those skilled in the art.

These materials may be assembled with the transducer using the aforementioned techniques and in particular by adhesion. To facilitate bonding and to guarantee the strength of the bond, it will be preferable to use in this case an adhesive having a chemical nature identical to that of the material to be fixed, such as for example a silicone adhesive, a polyurethane adhesive or a hot-melt adhesive based on an acrylic triblock or ABA copolymer in order to assemble a silicone gel, a polyurethane gel or a material based on triblock copolymers and a plasticizer, respectively.

According to one embodiment, if it is desired to apply a gel, or a material based on a triblock copolymer and a plasticizer, to both faces of the transducer of the sensor, the latter may be encapsulated, for example by molding, in said gel or said material.

Finally, to facilitate contact between the sensor and the skin, an adhesive gel can be applied directly to the transducer. Such a gel may especially be a silicone gel or an adhesive based on a compound consisting of a triblock copolymer, a plasticizer and a tackifying resin.

According to another embodiment, the sensor may be used as such, if it has a suitable compression elastic modulus, without adding any further material, on the face of the transducer which comes into contact with the skin.

As an example of such sensors, mention may be made of a Hall-effect sensor, the transducer of which takes the form of a monolayer block of cellular material, for example an ethylene/vinyl acetate foam, filled with magnetic particles for converting the applied pressure into a measurable electrical quantity.

In the case of such a sensor comprising a monolayer transducer, it will be preferential to use a sensor in which the transducer has a thickness of between 0.5 and 4.5 mm, preferably between 1 and 3 mm.

The Electronic System

The interface pressure measurement system according to the invention also includes an electronic system connected to the pressure sensors and capable of acquiring the values measured simultaneously by these sensors.

It is the acquisition of these values that makes it possible in particular for the differential pressure exerted by the compression system, and consequently the effectiveness thereof, to be controlled at any moment.

In the context of the present invention, the term "electronic system" is understood to mean all of the elements used to allow the necessary energy and data streams to be exchanged in order to manage the measurements carried out by the pressure sensors.

In general, this electronic system comprises:
- at least one processing unit comprising a microcontroller and a memory, said processing unit being capable of acquiring and of processing the signals representative of the values measured by the pressure sensors; and
- at least one power supply circuit comprising an energy source and an energy converter/distributor device.

According to a currently preferred embodiment of the invention, this electronic system comprises:
- an onboard device connected to the supporting member, preferably by being fixed thereto, and serving for the acquisition and processing of the values measured by the pressure sensors, said device comprising means for transmitting said values measured by the sensors; and
- a remote device comprising:
  - communication means compatible with the transmission means of the onboard device and at least transmitting the data from the onboard device to the remote device and
  - a processing circuit connected to a display device.

Figure 3:
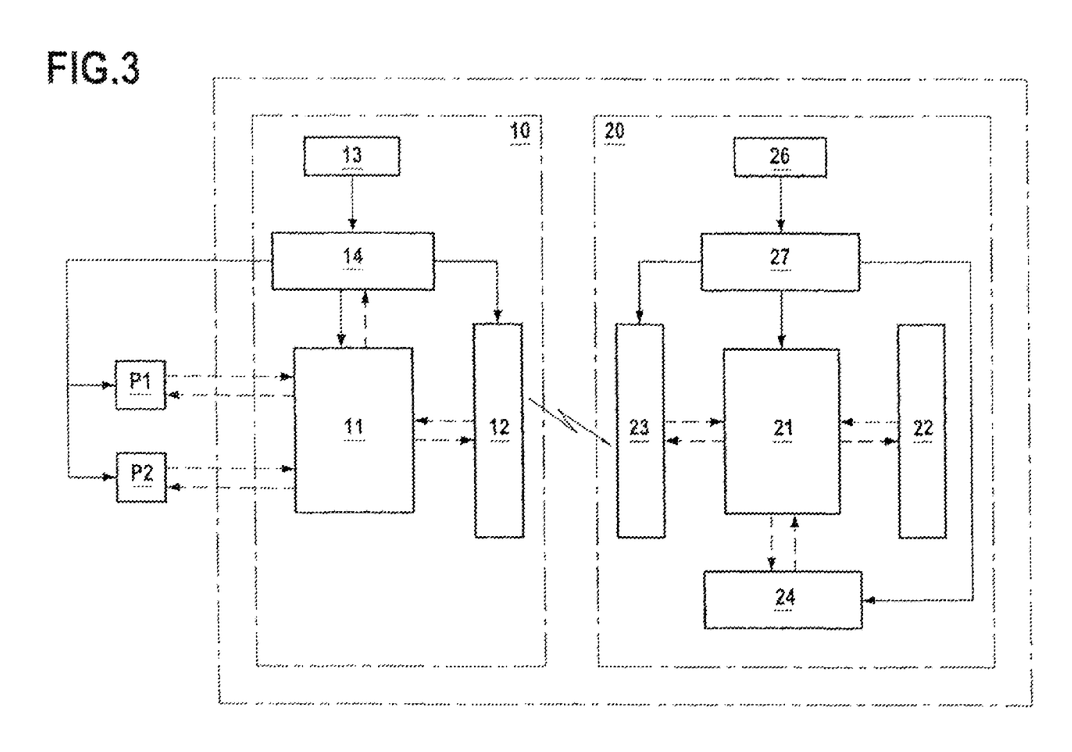
FIG. 3 schematically illustrates the architecture of the electronic system of the interface pressure measurement system according to the invention.

The general architecture of this preferred electronic system is illustrated in FIG. 3.

The onboard device 10 comprises a processing unit 11 comprising a microcontroller and transmission means 12 for transmitting said values measured by the pressure sensors $P_1$ and $P_2$, and also a power supply circuit comprising an energy source 13 and an energy converter/distributor device 14.

The microcontroller of the processing unit 11, integrates, filters, processes and digitizes the raw signals put out by the pressure sensors $P_1$ and $P_2$. It performs the analog/digital conversion of these signals. It may also analyze these signals by Fourier transforms or digital filters may be used that are combined with software for checking the data in certain events. It stores the standardization and calibration data from the pressure sensors and the data measured by these sensors. It controls the transmission of the data to the remote device and correctly manages the energy distribution via the energy converter/distributor device 14.

In the context of the present invention, any type of microcontroller (or microprocessor) commonly employed in the construction of electronic and microelectronic systems may be used. Such products are for example sold by the companies Texas Instruments, Microchip and NXP under the names 8150, 16F690 and Coolflux respectively.

The remote device 20 comprises a processing unit 21 comprising a microcontroller, a memory 22, communication means 23 compatible with the transmission means 12 of the onboard system, a display device 24 and a power supply circuit comprising an energy source 26 and an energy converter/distributor device 27.

Communication between the onboard system and the remote system may be by wire or wireless (radio module and antenna) as in the example shown.

The Energy Source

In the context of the present description, the term "energy source" is understood to mean any device capable of delivering sufficient energy to power all the elements of the interface pressure measurement system (sensors and electronic system).

In the case of a wire system, this energy may be delivered for example from an electrical socket via a wire.

In the case of a wireless system, any type of energy source commonly employed in measurement instruments may be used, such as in particular disposable batteries, rechargeable batteries or devices capable of collecting energy from their environment, these being denoted by the term "scavengers". A scavenger may especially collect solar energy or the energy produced by temperature gradients, vibrations, movements, especially the movement of a person, or electromagnetic phenomena. A scavenger converts the energy thus collected into electrical (voltage, frequency, etc.) data. This energy may be stored in a battery or a supercapacitor that may be incorporated into the interface pressure measurement system.

The Communication Means

According to a currently preferred embodiment of the invention, the communication between the onboard device and the remote device could be wireless communication and preferably radiofrequency communication.

The communication means generally comprise a communication module that incorporates the electronics for carrying out the communication and an antenna with suitable software and hardware.

The communication module of the onboard device may be:
- unidirectional, in this case merely transmitting to the outside the data delivered by the sensors and the microcontroller; or
- bidirectional (transmitter/receiver), in this case it also receives data coming from the outside, as in the example shown.

The wireless communication may possibly be performed in two steps.

In a first step, data communication takes place between the onboard system and a portable control module. The latter may for example take the form of a wrist watch or a device of the portable telephone type. In this case, the range between the system and the module will probably be of the order of 10 meters and the maximum data rate less than 1 kilobyte per second. Advantageously, the communication will be radiofrequency communication (for example at a frequency of 2.4 GHz) and may especially use for this purpose the communication module sold by Nordic Semiconductor under the reference nRF24L01. Alternatively, the communication may also be performed by inductive coupling, with the corresponding advantage of a very low level of interference with the human body, and it is possible to use for this purpose the communication module sold by NXP under the reference "Coolflux radio module".

In a second step, communication takes place between this portable control module and a computer. In this case it will be preferable to use a radiofrequency link at 2.45 GHz, enabling a greater volume of data to be transferred and over longer distances. In this case, the data rate is of the order of 1 Mbyte per second and the range of the order of one hundred meters. Various devices may be used for this purpose. For example, the Zigbee®, Bluetooth® and Wifi® protocols may be mentioned.

Two-step communication is particularly suitable for use of the interface pressure measurement system according to the invention by the clinical staff or even by the patient himself.

The portable control module serves to control the system and to record data. This data may be exploited subsequently by the clinician on his computer so as to adapt the treatment and check the patient's observance therewith.

Of course, direct data communication between the onboard system and a computer is also conceivable.

When radiofrequency communication is used, the onboard device includes an antenna. This may have various configurations depending on the frequency used, the waveform of the signal to be processed and the available energy.

In general, a copper or aluminum antenna will be used, but it is also possible to use an antenna formed from a conductive ink.

According to a preferred embodiment, the antenna takes the form of a cylindrical coil wound around a ferrite core (with a diameter of 4 mm or less) or a flat coil in the form of a snail shell (with a diameter of 10 mm or more).

Like the other components of the onboard device, the antenna may be fixed to a rigid or flexible printed circuit with these other components, or may be fixed isolatedly onto the support. Likewise, it may be encapsulated isolatedly or with these other components.

If the supporting member is extensible, it will be preferable to fix the antenna directly on this support or on an extensible circuit, as will be described later, for example on an extensible polyurethane film.

Figure 4A:
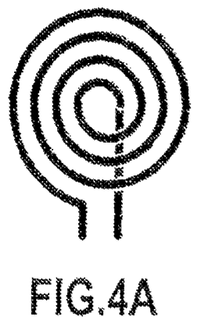
FIGS. 4A to 4C illustrate various embodiments of antennas that can be used in the aforementioned electronic system.
Figure 4B:
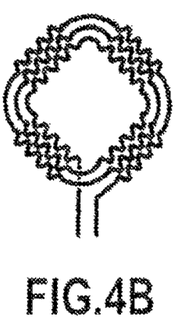
Figure 4C:
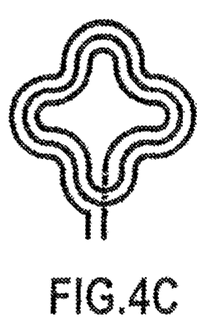
Figure 5A:
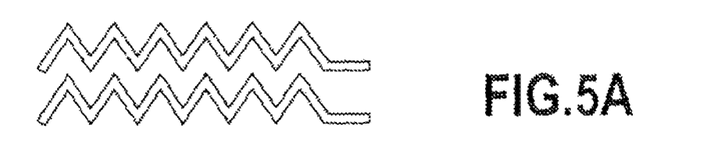
FIGS. 5A to 5D illustrate various embodiments of a moisture sensor or detection system that can be used in the context of the invention.
Figure 5B:
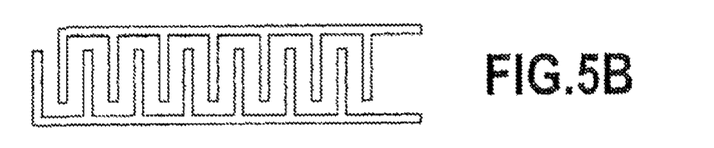
Figure 5C:
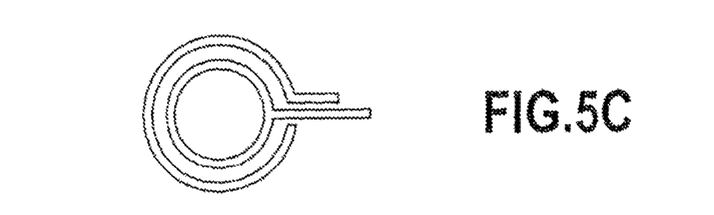
Figure 5D:
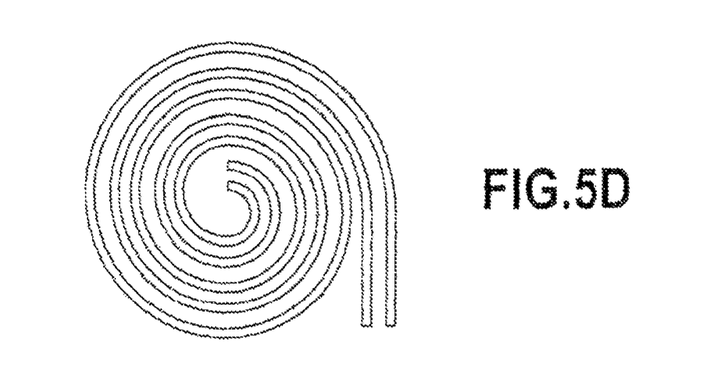

FIGS. 4A, 4B and 4C illustrate various shapes of antenna that may be placed directly on the extensible support.

The Conducting Tracks

According to a currently preferred embodiment, the onboard device will be connected to the pressure sensors by conducting tracks.

If the supporting member is not extensible, the conducting tracks may be produced by techniques well known to those skilled in the art such as, in particular, by screen printing using a conductive ink, for example a silver-based ink or one based on a silver-copper alloy.

These techniques may also be used when said support is extensible.

The conducting tracks may also be integrated into the supporting member when this takes the form of a sheet of extensible polymer, for example a silicone or polyurethane gel.

Alternatively, conducting tracks, for example made of copper, may be formed on the supporting member when this takes the form of a film, for example a polyurethane film. In practice, this may be accomplished by covering a sheet of copper on one of its sides with a polyurethane film, applying a mask on the uncovered side of the sheet (the solid parts of said mask taking the form of the tracks to be obtained) and destroying the unmasked copper by acid etching.

When the supporting member is extensible, it is important for there to be no break in these conducting tracks when the supporting member is extended. For this purpose, the tracks will preferably take the form of a succession of $\Omega$-shaped elements connected in succession pairwise. When the supporting member extends, each $\Omega$-shaped element may deform longitudinally, thus preventing the track from breaking. Such $\Omega$-shaped structures are for example described in the patent application WO 2004/107973.

Alternatively, it is possible to avoid the risk of breakage by fixing extension limiters to the extensible supporting member.

These extension limiters may for example consist of stiffening strips. These strips will be formed from a material having a lower extensibility than that of the extensible supporting member. Thus, when the supporting member is stretched, it will be "blocked" by said strips above a certain extension. Preferably, these strips will have a longitudinal extensibility of around 20% or less. The materials that can be used to produce these strips may be similar to those mentioned for the supporting member, in particular they may be fabrics, foams or films. These strips may be fixed to the extensible support by conventional techniques adapted to the nature of the supporting member. As examples of such techniques, mention may be made of tacking or needling, in the case of a fabric supporting member, such as for example a nonwoven, or in the case of a foam; in the case of a supporting member in film form, ultrasonic welding, bonding, thermal complexing or fixing using an adhesive.

The extension limiters may also consist of one or more wires integrated into the plane of the supporting member, over all or part of the latter, in a sinusoidal wave configuration and having a tensile strength greater than that of the supporting member. Thus, when the supporting member is stretched, the wire becomes taut and stops the supporting member from extending. Said wire or wires may be integrated into or fixed to the extensible supporting member using the techniques described above for fixing the strips.

In general, all the components of the onboard device will be positioned between the two pressure sensors so as to reduce the risk of breaking the conducting tracks placed on the supporting member. The shorter these tracks, the lower the risk of breakage.

Figure 2:
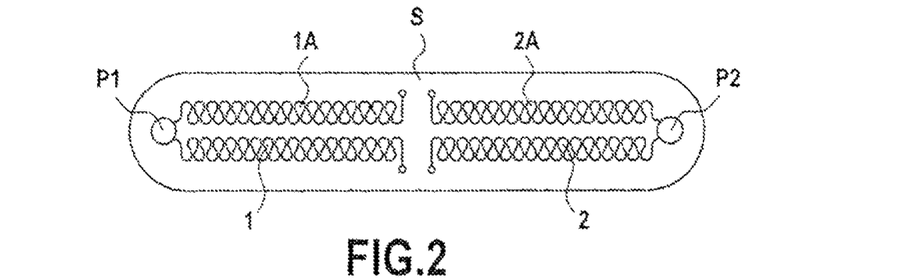
FIG. 2 illustrates a supporting member provided with conducting tracks according to one embodiment of the invention.

FIG. 2 shows one embodiment of a supporting member S comprising two series of conducting tracks 1, 1A and 2, 2A formed from $\Omega$-shaped elements and intended to be connected to the pressure sensors $P_1$ and $P_2$, respectively.

The Connections

The functional elements of the onboard device and the sensors will be connected to the conducting tracks of the supporting member by the conventional techniques used in the case of nonextensible supporting members.

These connections may be conventional soldered joints or else produced:
- either using Z-shaped conductive adhesives such as, for example, the adhesives sold by Adhesive Research under the names ARcare 90366 or ARcare 90447;
- or using conductive adhesives in the form of adhesive-coated foam, conductive glues or conducting polymers such as, for example, the products sold by Dow Corning and Emerson and Cummings under the names DA 65224 and XCS 80091 respectively;
- or else using conductive Velcro.

Such connections will connect the conducting pads of said functional elements and of the sensors to the conducting pads placed on the conducting tracks of the supporting member.

Alternatively, these connections may be made using microconnectors, widely used to make connections in computers or mobile telephones.

When the measurement system is a disposable system, inviolable connections such as soldered joints may be used.

However, when the measurement system is intended to be partly reused, it will be preferable to use "reactivable" connections such as, for example, connections made using adhesives or microconnectors. In this case, the supporting member may be discarded after use and the functional elements reused with a new supporting member to which said elements will be fixed by means of new adhesives or microconnectors. Alternatively, only certain functional elements of the system may be reused, for example when it is desired to change the sensors or the energy source.

When the measurement system is intended to be entirely reused, all the functional elements of the system (sensors and onboard system) may be encapsulated or embedded, like conventional electronic devices, in silicone or polyurethane polymers or in adhesives, as described for example in the patent application WO 2006/094513. In this case, a system will be obtained that can be cleaned after use and can be reused many times.

In the context of the present invention, it is preferred to encapsulate only the more sensitive elements, and in particular the electronic components, so as not to impair the "breathing" properties of the system.

Likewise, so as not to restrict the extensibility of the supporting member, it is also preferable to encapsulate only the connections between the electronic components and the extensible supporting member.

The various components of the onboard device (energy source, antenna, microprocessor) and the conducting tracks connecting them, may, depending on their nature and their size, be connected directly to the pads produced on the extensible supporting member or assembled on one or more "interposing" elements or printed circuits that will be connected to the pads of the extensible supporting member.

Alternatively, some of these elements, such as the energy source or the antenna, may be connected directly, or via interposing elements, on a prolongation of the support, beyond the part extending between the pressure sensors, so as not to impair the extensibility of the supporting member. This prolongation of the supporting member is not necessarily extensible.

As indicated above, this prolongation of the supporting member and the elements that are connected thereto may be encapsulated in a suitable material, such as a silicone based for example on a polydimethylsiloxane.

The materials that can be used to produce the interposing elements on which the electronic components are assembled are those that are commonly used for producing conventional electronic circuits. Even though it is possible to use rigid materials, it will nevertheless be preferred to use for this purpose flexible, pliant or conformable semi-rigid materials so as to adapt to the patient's morphology and to the critical radius of curvature of an ankle, which is around 25 mm.

Among the materials that can be used for producing these pliant or semi-rigid interposing elements, mention may be made of polyimides such as, for example, the products sold by DuPont under the name Kapton® and epoxy films having a thickness of around 0.1 to 0.4 mm such as the products sold under the term "epoxy FR4".

If necessary, and in particular in the context of treating leg ulcers, a lacquer may be applied to the surface of these interposing elements so as to avoid any short circuit or electrical malfunction that could be caused by contact with the exudates of the wound or with moisture in the dressing beneath the bandage during use of the interface pressure measurement system. Lacquers that can be used for this purpose are for example the products Propocure for example of the 520-530 series, sold by APCIS.

The Other Sensors

According to variant embodiments, the interface pressure measurement system according to the invention may comprise sensors other than pressure measurement sensors, so as to measure additional parameters useful in the context of compression therapy treatment, such as acceleration (to detect and evaluate the physical activity of the patient), temperature (which plays an important role in venous circulation) and moisture (for detecting sweating beneath the bandage and problems due to the level of wound exudation in the case of leg ulcers).

Of course, other parameters may be evaluated such as, for example, the pH using physiochemical sensors.

Preferably, so as not to impair the extensibility properties of the interface pressure measurement system, these sensors will be positioned on a prolongation of the supporting member, beyond the part extending between the pressure sensors. This prolongation of the supporting member may or may not be extensible.

In the context of treating leg ulcers, detection of the degree of moisture of the dressing that covers the wound and is concealed beneath the bandage is an important factor for promoting sufficient observance with the treatment and to ensure that the treatment is effective.

Many known devices for detecting moisture (or moisture sensors) exist.

In the context of the present invention, it is preferable, however, to use a system consisting of two electrodes (one acting as anode and the other as cathode) spaced apart by a distance of a few millimeters (preferably 2 to 20 millimeters and more preferably 2 to 5 millimeters). This spacing will be adapted according to the desired objectives: detection threshold; location on the extensible supporting member; size of the dressing and of the extensible supporting member, and according to the patient's morphology.

These electrodes may consist of various materials that will be deposited, like the conducting tracks, on the supporting member. Advantageously, they will be electrodes formed from copper tracks, the surface of which may or may not have been subjected to a chemical or electrolytic treatment, with an addition of gold or platinum, or else electrodes obtained by screen printing using conductive inks, such as inks filled with a silver salt, carbon, etc.

If the support is formed from a fabric material, electronically conducting fibers may also be used as electrodes.

The length, width and configuration of these electrodes may vary. Thus, two parallel sinusoidal electrodes, two mutually imbricated combs, two concentric rings or even two parallel spirals may be conceived. Such configurations are shown in FIGS. 5A, 5B, 5C and 5D respectively.

Figure 6:
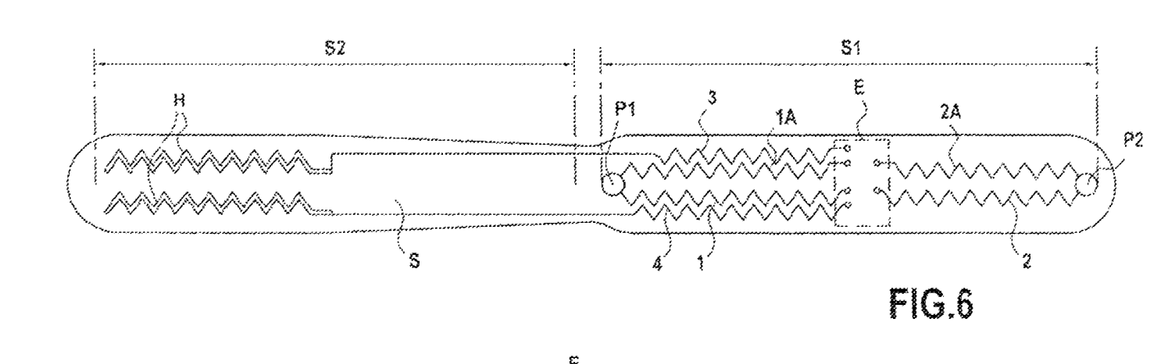
FIG. 6 illustrates one embodiment of an interface pressure measurement system that includes a moisture detection system.

These two electrodes may be connected to the electronic system via conducting tracks 3, 4, as shown in FIG. 6.

The measurement principle of such a moisture detector is based on the change in resistivity between the anode and the cathode upon hydration.

This resistivity value will be compared with a calibrated value according to the detection threshold adopted, this being recorded in the electronic system.

Analysis of this comparison may then trigger an alarm, for example a visual alarm (LED) or an audible alarm (a buzzer), or a change of state by one bit if the electronic system incorporates a microprocessor.

The alarm may for example be located on the portable control module described above.

Another important parameter to evaluate in the context of compression therapy may be the temperature.

The temperature may be measured conventionally using a temperature sensor, such as a thermistor, the resistance of which varies according to the temperature.

Such temperature sensors are well known to those skilled in the art and used in the fabric field.

Both the shape and the configuration of the interface pressure measurement system according to the present invention may vary.

Figure 7:
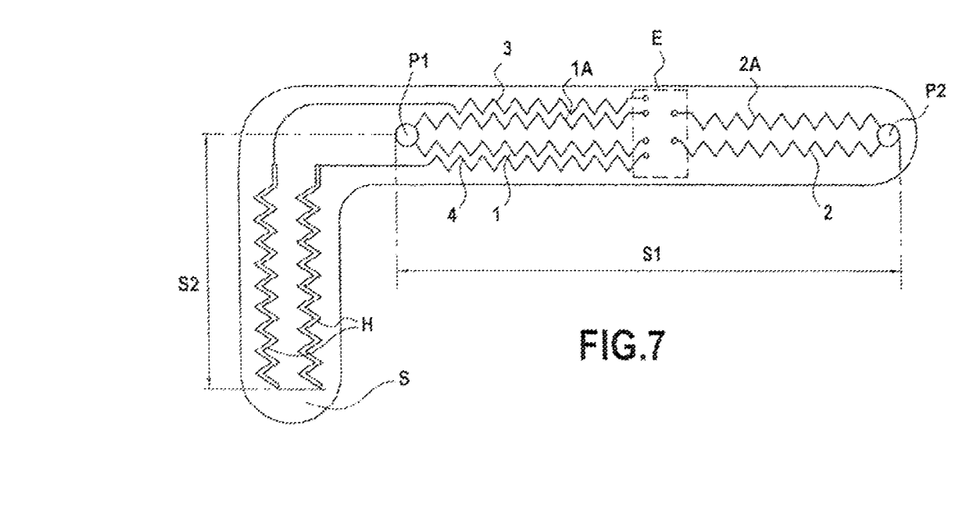
FIG. 7 illustrates another embodiment of the interface pressure measurement system shown in FIG. 6.

In the context of the present invention, and in particular for the treatment of leg ulcers by compression therapy, two particular shapes illustrated in FIGS. 6 and 7 are preferred.

The first shape, of the "stocking" type, is shown schematically in FIG. 7.

The supporting member S comprises:
- a first part S1 extending substantially longitudinally and bounded by the two pressure sensors $P_1$ and $P_2$ to be positioned on the points $B_1$ and C (see FIG. 1), for example on the external surface of the leg; and
- a second part S2 extending the first part substantially perpendicularly and comprising the two electrodes H forming the moisture detector, which second part is intended to be folded over in the use position on the inside of the leg so as to cover the upper surface of the dressing positioned on the leg ulcer.

In the example shown, the components of the onboard device (energy source, communication module, antenna, microprocessor) are assembled on a single printed circuit E placed between the two sensors $P_1$ and $P_2$. This arrangement is particularly advantageous since it maximizes, when the supporting member S is extended, the integrity of the conducting tracks 1, 1A and 2, 2A supplying power to the sensors $P_1$ and $P_2$ and the integrity of the tracks 3 and 4 supplying power to the electrodes H.

This "stocking" shape requires two separate (left and right) versions to be produced, depending on the leg to be treated.

The second shape is shown schematically in FIG. 6.

The two parts S1 and S2 forming the supporting member are aligned here so that this single shape is suitable whatever leg (left or right leg) is to be treated.

Figure 1A:
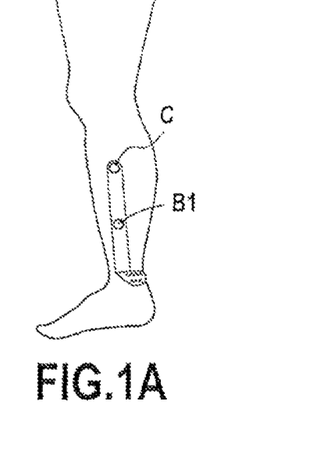
FIG. 1A is a figure similar to FIG. 1, illustrating an interface pressure measurement system according to another embodiment of the invention, placed on a leg.

The supporting member may, be folded in the region separating its two constituent parts S1 and S2, thus enabling the moisture detector to be positioned, in use, on the left-hand side or right-hand side depending on the leg treated (see FIG. 1A). The fold may therefore be advantageously sized according to the size of the patient's leg and to the location of the wound.

Likewise, the length of the electrodes forming the moisture measurement device makes it possible to measure, if necessary, the excess moisture on the external surface of the dressing and/or on the periphery of the latter should exudates be released via the edges of the dressing.

Of course, the moisture detector may be replaced with a temperature sensor with any other type of sensor.

According to one embodiment, a moisture detector and a temperature sensor may be placed on the second part S2 of the supporting member.

According to another embodiment, it is possible to place a moisture detector on the second part S2 of the supporting member and a temperature sensor on a third part of the supporting member (not shown) forming a prolongation of the first part S1 of the supporting member on the opposite side to the second part.

As indicated above, the second and third parts of the supporting member may or may not be extensible. However, to facilitate manufacture, it will be preferable to use a supporting member which is extensible over its entire length.

The interface pressure measurement system according to the invention may be fixed to the limb to be treated using any known means for fixing a device to the human body, such as a Velcro-type fastener or an adhesive.

In the context of compression therapy treatment, it will be most particularly preferable to use a non-traumatizing adhesive, if necessary able to be repositioned in the same way as those commonly employed for producing absorbent dressings intended to be positioned on the skin or on leg ulcers. This adhesive may for example cover, completely or partially, that surface of the supporting member of the system which will come into contact with the skin or the wound. The reader may for example refer to the patent application WO 2006/094513 for the choice of such an adhesive. If necessary, this adhesive may serve for encapsulating some or all of the components of the interface pressure measurement system.

The invention claimed is:

1. A system for measuring an interface pressure exerted on skin, comprising:
   a supporting member;
   at least two pressure sensors placed apart on the supporting member, the at least two pressure sensors configured to measure a pressure being exerted at two locations in a use position, wherein at least one of the two locations is predetermined; and
   an electronic system connected to the at least two pressure sensors and configured to acquire values simultaneously measured by the at least two pressure sensors,
   wherein each of the at least two pressure sensors includes:
      a transducer element, said transducer element having a surface configured to contact with the skin in the use position, either directly or via an intermediate layer of a material covering said surface of the transducer element, and
      a compressive elastic modulus of the surface of said transducer element is between 30 and 500 kPa when the surface of the transducer element is configured to contact with the skin directly.

2. The measurement system as claimed in claim 1, wherein said material constituting said intermediate layer is selected from the group consisting of cellular materials, gels and compounds based on thermoplastic polymers.

3. The measurement system as claimed in claim 1, wherein each pressure sensor is substantially flat and selected from the group consisting of resistive sensors, piezoelectric sensors, Hall-effect magnetic sensors and capacitive sensors.

4. The measurement system as claimed in claim 1, wherein the electronic system includes:
   an onboard device connected to the supporting member, and the onboard device configured for acquisition and processing of the values measured by the at least two pressure sensors, said device configured to transmit said values measured by the at least two pressure sensors; and
   a remote device including:
      a communication circuit configured to transmit data from the onboard device to the remote device; and
      a processing circuit connected to a display device.

5. The measurement system as claimed in claim 1, wherein the supporting member is formed from a material selected from the group consisting of fabric materials, cellular materials, materials in film form and a combination thereof.

6. The measurement system as claimed in claim 1, wherein the supporting member is nonocclusive, and has a water vapor permeability that is equal to or greater than 1000 g/m$^2$/24 h.

7. The measurement system as claimed in claim 6, wherein the supporting member is made of a nonwoven or a polyurethane film.

8. The measurement system as claimed in claim 1, wherein the supporting member is extensible and has an extensibility of around 10 to 20% in a longitudinal direction and around 3 to 12% in a transverse direction.

9. The measurement system as claimed in claim 1, wherein the supporting member further includes:
at least one moisture sensor; and/or
at least one temperature sensor.

10. The measurement system as claimed in claim 4, wherein the onboard device is fixed to the supporting member and placed between the at least two pressure sensors.

11. The measurement system as claimed in claim 9, the moisture sensor and/or temperature sensor are/is placed on the supporting member external to a space defined between the at least two pressure sensors.

12. A restraint kit, comprising:
a restraint system; and
the system according to claim 1.

13. A system for measuring an interface pressure exerted on skin in compression therapy, comprising:
a supporting member;
at least two pressure sensors placed apart on the supporting member, the at least two pressure sensors configured to measure a pressure being exerted at two locations in a use position, wherein at least one of the two locations is predetermined; and
an electronic system connected to the at least two pressure sensors and configured to acquire values simultaneously measured by the sensors,
wherein each of the at least two pressure sensors includes:
a substantially flat transducer element, said transducer element having a surface configured to contact with the skin in the use position, either directly or via an intermediate layer of a material covering said surface of the transducer element, and
a compressive elastic modulus of the surface of said transducer element is between 30 and 500 kPa when the surface of said transducer is configured to contact with the skin directly.

14. The measurement system as claimed in claim 1, wherein the compressive elastic modulus is between 80 and 400 kPa.

15. The measurement system as claimed in claim 1, wherein the compressive elastic modulus is between 200 and 400 kPa.

16. The measurement system as claimed in claim 1, wherein said material constituting said intermediate layer is selected from the group consisting of cellular materials, hydrophobic silicone gels or hydrophobic polyurethane gels and compounds based on hydrophobic thermoplastic polymers;
wherein the cellular materials are selected from the group consisting of hydrophobic foams, foams made of crosslinked polyethylene or foams made of polyurethane, silicone, polyvinyl chloride, ethylene-propylene diene copolymer and neoprene; and
the compounds based on hydrophobic thermoplastic polymers are selected from the group consisting of triblock polymers and a plasticizer.

17. The measurement system as claimed in claim 10, wherein the moisture sensor and/or temperature sensor are/is placed on the supporting member external to a space defined between the at least two pressure sensors.

18. The measurement system as claimed in claim 10, wherein the moisture sensor and/or temperature sensor are/is placed on the supporting member external to a space defined between the at least two pressure sensors in a part extending the supporting member along an axis defined by the at least two pressure sensors or along an axis perpendicular thereto.

19. The measurement system as claimed in claim 13, wherein each pressure sensor is substantially flat and selected from the group consisting of resistive sensors, piezoelectric sensors, Hall-effect magnetic sensors and capacitive sensors.

20. The measurement system as claimed in claim 13, wherein the electronic system comprises:
an onboard device connected to the supporting member, and the onboard device configured for acquisition and processing of the values measured by the at least two pressure sensors, said device configured to transmit said values measured by the at least two pressure sensors; and
a remote device including:
a communication circuit configured to transmit data from the onboard device to the remote device; and
a processing circuit connected to a display device.

21. The measurement system as claimed in claim 13, wherein the compressive elastic modulus is between 80 and 400 kPa.

22. The measurement system as claimed in claim 13, wherein the compressive elastic modulus is between 200 and 400 kPa.

23. The measurement system as claimed in claim 13, wherein said material constituting said intermediate layer is selected from the group consisting of cellular materials, hydrophobic silicone gels or hydrophobic polyurethane gels and compounds based on hydrophobic thermoplastic polymers;
wherein the cellular materials are selected from the group consisting of hydrophobic foams, foams made of crosslinked polyethylene or foams made of polyurethane, silicone, polyvinyl chloride, ethylene-propylene diene copolymer and neoprene; and
the compounds based on hydrophobic thermoplastic polymers are selected from the group consisting of triblock polymers and a plasticizer.

24. The system according to claim 1, wherein the compressive elastic modulus of said intermediate layer covering the surface is between 30 and 500 kPa when the transducer element is configured to contact with the skin via the intermediate layer.

25. The system as claimed in claim 24, wherein said material constituting said intermediate layer is selected from the group consisting of cellular materials, gels and compounds based on thermoplastic polymers.

26. The system according to claim 24, wherein each pressure sensor is substantially flat and selected from the group consisting of resistive sensors, piezoelectric sensors, Hall-effect magnetic sensors and capacitive sensors.

27. The system according to claim 24, wherein the electronic system includes:
an onboard device connected to the supporting member, and the onboard device configured for acquisition and processing of the values measured by the at least two pressure sensors, said device configured to transmit said values measured by the at least two pressure sensors; and
a remote device including:
- a communication circuit configured to transmit data from the onboard device to the remote device; and
- a processing circuit connected to a display device.

28. The system according to claim 24, wherein the supporting member is formed from a material selected from the group consisting of fabric materials, cellular materials, materials in film form and a combination thereof.

29. The system according to claim 24, wherein the supporting member is nonocclusive, and has a water vapor permeability that is equal to or greater than 1000 g/m$^2$/24 h.

30. The system according to claim 29, wherein the supporting member is made of a nonwoven or a polyurethane film.

31. The system according to claim 24, wherein the supporting member is extensible and has an extensibility of around 10 to 20% in a longitudinal direction and around 3 to 12% in a transverse direction.

32. The system according to claim 24, wherein the supporting member further includes:
- at least one moisture sensor; and/or
- at least one temperature sensor.

33. The system according to claim 27, wherein the onboard device is fixed to the supporting member and placed between the at least two pressure sensors.

34. The system according to claim 32, the moisture sensor and/or temperature sensor are/is placed on the supporting member external to a space defined between the at least two pressure sensors.

35. A restraint kit, comprising:
- a restraint system; and
- the system according to claim 24.

36. The system according to claim 13, wherein the compressive elastic modulus of said intermediate layer is between 30 and 500 kPa when the surface of said transducer element is configured to contact the skin via the intermediate layer.

37. The system according to claim 24, wherein the compressive elastic modulus is between 80 and 400 kPa.

38. The system according to claim 24, wherein the compressive elastic modulus is between 200 and 400 kPa.

39. The system according to claim 24, wherein said material constituting said intermediate layer is selected from the group consisting of cellular materials, hydrophobic silicone gels or hydrophobic polyurethane gels and compounds based on hydrophobic thermoplastic polymers;
wherein the cellular materials are selected from the group consisting of hydrophobic foams, foams made of crosslinked polyethylene or foams made of polyurethane, silicone, polyvinyl chloride, ethylene-propylene diene copolymer and neoprene; and
the compounds based on hydrophobic thermoplastic polymers are selected from the group consisting of triblock polymers and a plasticizer.

40. The system according to claim 33, wherein the moisture sensor and/or temperature sensor are/is placed on the supporting member external to a space defined between the at least two pressure sensors.

41. The system according to claim 33, wherein the moisture sensor and/or temperature sensor are/is placed on the supporting member external to a space defined between the at least two pressure sensors in a part extending the supporting member along an axis defined by the at least two pressure sensors or along an axis perpendicular thereto.

42. The system according to claim 36, wherein each pressure sensor is substantially flat and selected from the group consisting of resistive sensors, piezoelectric sensors, Hall-effect magnetic sensors and capacitive sensors.

43. The system according to claim 36, wherein the electronic system comprises:
an onboard device connected to the supporting member, and the onboard device configured for acquisition and processing of the values measured by the at least two pressure sensors, said device configured to transmit said values measured by the at least two pressure sensors; and
a remote device including:
- a communication circuit configured to transmit data from the onboard device to the remote device; and
- a processing circuit connected to a display device.

44. The system according to claim 36, wherein the compressive elastic modulus is between 80 and 400 kPa.

45. The system according to claim 36, wherein the compressive elastic modulus is between 200 and 400 kPa.

46. The system according to claim 36, wherein said material constituting said intermediate layer is selected from the group consisting of cellular materials, hydrophobic silicone gels or hydrophobic polyurethane gels and compounds based on hydrophobic thermoplastic polymers;
wherein the cellular materials are selected from the group consisting of hydrophobic foams, foams made of crosslinked polyethylene or foams made of polyurethane, silicone, polyvinyl chloride, ethylene-propylene diene copolymer and neoprene; and
the compounds based on hydrophobic thermoplastic polymers are selected from the group consisting of triblock polymers and a plasticizer.

* * * * *